United States Patent
Bandyopadhyay et al.

(10) Patent No.: US 6,610,332 B2
(45) Date of Patent: Aug. 26, 2003

(54) ANTI-LEISHMANIAL ACTIVITY OF BETEL LEAF EXTRACT

(75) Inventors: Santu Bandyopadhyay, Calcutta (IN); Bikash Pal, Calcutta (IN); Samir Bhattacharya, Calcutta (IN); Mitali Ray, Calcutta (IN); Keshab Chandra Roy, Calcutta (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/124,459

(22) Filed: Apr. 18, 2002

(65) Prior Publication Data

US 2002/0150636 A1 Oct. 17, 2002

Related U.S. Application Data

(62) Division of application No. 09/772,031, filed on Jan. 30, 2001, now abandoned.

(30) Foreign Application Priority Data

Dec. 4, 2000 (WO) ................................. PCT/IN00/00119

(51) Int. Cl.$^7$ ............................................... A61K 35/78
(52) U.S. Cl. ........................ 424/769; 424/774; 424/725
(58) Field of Search ................................. 424/769, 774, 424/725

(56) References Cited

U.S. PATENT DOCUMENTS 5,389,371 A 2/1995 Shiao

OTHER PUBLICATIONS

Database WPI, Section CH, Week 199930, Derwent Publications LTD., London, BG; AN 1999–352797, XP002174279 (JP 11 130685 A).

Database WPI, Section CH, Week 199702, Derwent Publications LTD., London, BG; AN 1997–017312, XP002174280 (JP 08 283171 A).

Mori H et al., "Carcinogenicity Examination of Betel Nuts and Piper Betel Leaves", Experientia (1979), vol. 35, No. 3, pp. 384–385. ISSN: 0014–4754, XP001008625.

Chakrabarti, G. et al., "Indolylquinoline Derivatives are Cytotoxic to *Leishmania donovani* Promastigotes and Amastigotes in vitro and are Effective in Treating Murine Visceral Leishmaniasis," *Journal of Antimicrobial Chemotherapy*, vol. 43., pp. 359–366 (1999).

Wealth of India, vol. 8, pp. 84–95, 1990.

Padma et al., Anticarcinogenic Effect of Betel Leaf Extract against Tobacco Carcinogens (1989), *Cancer Letts.*, vol. 45, pp. 195–202.

Azuine et al., Protective Single/Combined Treatment with Betel Leaf and Tumeric against Methyl (Acetoxymethyl) Nitrosamine–Induced Hamster Oral Carcinogenisis (1992), *Int. J. Cancer*, vol. 51, pp. 412–415.

Prabhu et al., Effect of Orally Administered Betel Leaf (Piper Betle Linn.) on Digestive Enzymes of Pancreas and Intestinal Mucosa and on Bile Production in Rats (Oct. 1995), *Indian Journal of Experimental Biology*, vol. 33, pp. 752–756.

Panda et al., Dual Role of Betel Leaf Extract on Thyroid Function in Male Mice (Dec. 1998), *Pharmacological Research*, vol. 38, No. 6, pp. 493–496.

*Primary Examiner*—Christopher R. Tate
(74) *Attorney, Agent, or Firm*—Fitzpatrick, Cella, Harper & Scinto

(57) ABSTRACT

This invention relates to method of treating visceral leishmaniasis or kala-azar by administering effective amount of betel leaf extract or lyophilized extract together with or associated with an additive and a composition comprising betel leaf extract with a pharmaceutically acceptable additive.

8 Claims, 1 Drawing Sheet

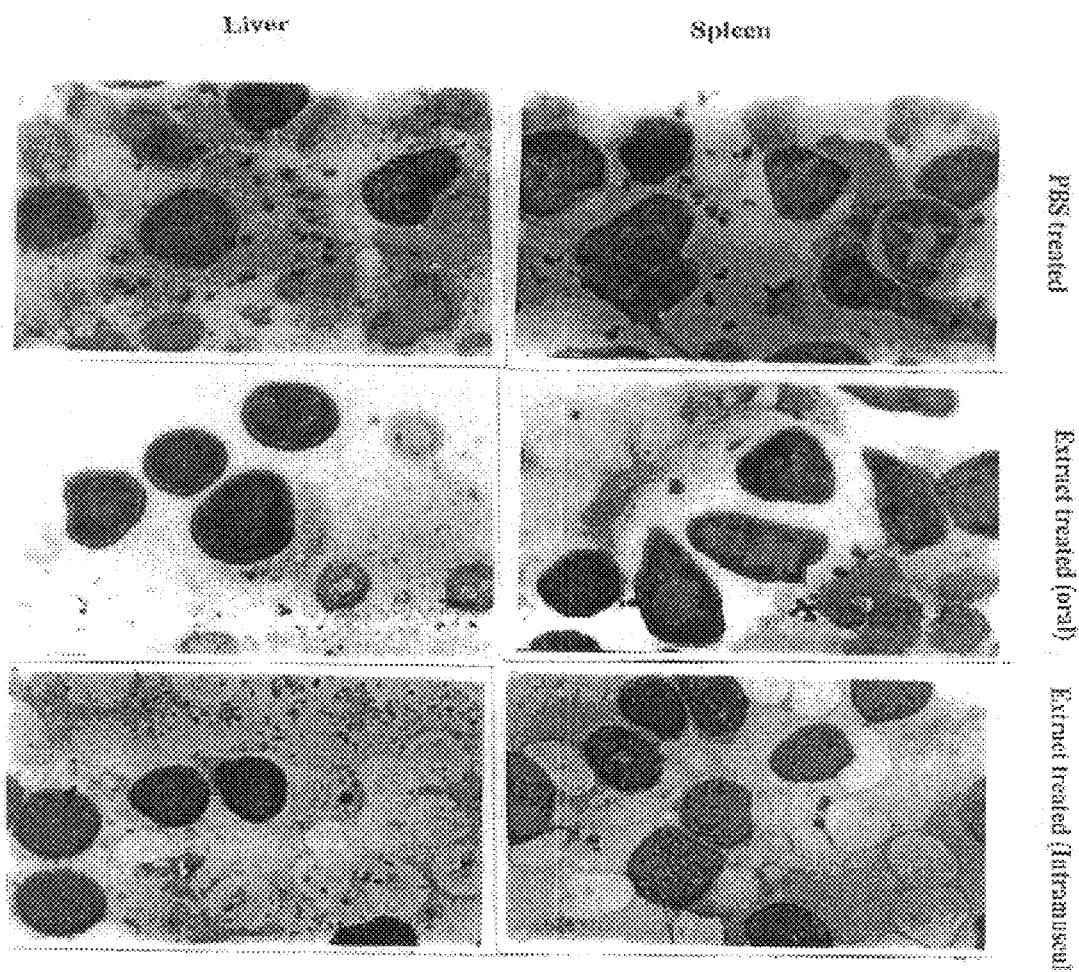
Fig. 1. Photomicrographs of Giemsa stained liver and spleen smears of *L. donovani* infected golden hamsters after treatment with PBS and betel leaf extract.

ANTI-LEISHMANIAL ACTIVITY OF BETEL LEAF EXTRACT

This application is a divisional of U.S. Application Ser. No. 09/772,031, filed Jan. 30, 2001, now abandoned.

FIELD OF INVENTION

This invention relates to the treatment of leishmaniasis in animals including human beings, preferably, the extract of betel leaf is used for the treatment of leishmaniasis in human beings. Chemotherapy for visceral leishmaniasis has seen little progress in recent years. Antileishmanicidal activity of betel leaf extracts suggests its potential use to treat human visceral leishmaniasis.

BACKGROUND AND PRIOR ART REFERENCES

Leishmaniasis commonly known as kala-azar as known in India is a global health problem. Infection by various species and strains of Leishmania causes a wide spectrum of disease in humans, with many different clinical presentations. The severity of the disease is largely dictated by the immunological status of the infected individual and by the species of Leishmania involved. Approximately 350 million people in 80 countries are estimated to be threatened by the disease. The World Health Organization (WHO) estimated 12 million cases of leishmaniasis worldwide, with over 400,000 new cases each year. The visceral form of leishmaniasis, or kala-azar, is caused by the parasite *Leishmania donovani* and is often fatal. Despite tremendous progress made in understanding the biochemistry and molecular biology of Leishmania species, treatment by chemotherapy has seen very little progress in recent years. The toxic pentavalent antimonials remain the mainstay of treatment for leishmaniasis. The second line drugs, pentamidine and amphotericin B, although used clinically, have serious toxic side effects. Therefore, improved drug therapy for leishmaniasis remains desirable. Indolylquinoline derivatives have recently been shown cytotoxic to *Leishmania donovani* promastigotes and amastigotes in vitro and are effective in treating murine visceral leishmaniasis (Ganes Chakrabarti, Anirban Basu, Partha Pratim Manna, Sashi Bhusahan Mahato, Nirup Bikash Mandal and Santu Bandyopadhyay, *Journal of Antimicrobial Chemotherapy* (1999) Vol. 43 pp.359–366).

Betel leaves have a strong pungent aromatic flavor and are widely used as a masticatory. Generally, mature or over mature leaves, which have ceased growing but not yet become brittle are used for chewing. The basic preparation for chewing purposes consists of betel leaf smeared with hydrated lime and catechu to which scrapings of arecanut are added; flavorings such as coconut shavings, clove, cardamom, fennel, powdered liquorice, nutmeg and also tobacco are used according to one's taste. In some places prepared pan is covered with silver or gold leaf. As a masticatory, it is credited with many properties: it is aromatic, digestive, stimulant and carminative. Medicinally, it is useful in catarrhal and pulmonary affections; it is also used for poultices. The effects of chewing of betel with arecanut and other adjuncts are the excitation of the salivary glands and the irritation of the mucous membrane of the mouth. The red coloration produced is due to a pigment in the arecanut, which manifests itself under the action of alkali in lime and catechu. A mild degree of stimulation is produced, resulting in a sensation of warmth and well being, besides imparting a pleasant odor. The most important factor determining the aromatic value of the leaf is the amount and particularly the nature of the essential oil present. Betel leaves from different regions vary in smell and taste. The most pungent is the Sanchi type, while the most mild and sweet ones are from Madras. The betel leaves contain essential oils, the content of oil varies from 0.7 to 2.6 per cent depending upon the varieties of leaves. The oil consists of phenols and terpens. The higher the proportion of phenol oil, the better the quality. An isomer of eugenol named chavibetol (betel phenol; 4-allyl-2-hydroxy-1-methoxy benzene) is considered to be the characteristic constituent of betel oil. It is however, absent in Indian samples. Betel oil of Indian types contain as a predominant phenolic constituent. Oil of betel has been used in the treatment of various respiratory catarrhs, as a local application either by gargle or by inhalation in diphtheria. It has carminative properties. It exhibits in different action on the central nervous system of mammals; lethal doses produce deep narcosis leading to death within a few hours. The essential oil and extracts of the leaves possess activity against several Gram-positive and Gram-negative bacteria such as *Micrococcus pyogenes* var. *albus* and var. *aureus, Bacillus subtilis* and *B. megaterium, Diplococcus pneumoniae, Streptococcus pyogenes, Escherichia coli, Salmonella typhosa, Vibrio comma, Shigella dysenteriae, Proteus vulgaris, Pseudomonas solanacaerum, Sarcina lutea* and *Erwinia carotovora*. The essential oil and leaf extracts also showed antifungal activity against *Asperigillus niger* and *A. oryzae, Curvularia lunata* and *Fusarium oxysporum*. The oil is found to be lethal in about 5 minutes to the protozoa *Paramaecium caudatum* (*Wealth of India*, Vol.8, pg.84–94).

OBJECTS OF THE INVENTION

The main object of the invention is to provide a method of treating animals including human beings for leishmaniasis by the way of administering betel leaf extract or lyophilized betel leaf extract.

Another object of the present invention is to provide a composition comprising betel leaf extract, which is useful for the treatment of leishmaniasis of human being.

Yet another object of the present invention is the preparation of the betel leaf water extract.

SUMMARY OF THE INVENTION

To meet the above objects, the invention provides use of betel leaf extract for the treatment of leishmaniasis in human beings and animals.

DETAILED DESCRIPTION

The present invention relates to a composition comprising betel leaf extract, which is useful for the treatment of leishmaniasis of human being and a process for the preparation of the betel leaf water extract. This invention also provides a method of treating the human being for leishmaniasis by the way of administering the extract or lyophilized extract as a composition comprising betel leaf extract along with a pharmaceutically acceptable additive.

Accordingly the invention provides a pharmaceutical composition useful for the treatment of visceral leishmaniasis, or kala-azar as known in India, said composition comprising effective amount of betel leaf extract or lyophilized extract together with or associated with a pharmaceutically acceptable additive.

In another embodiment the additive is selected in such a manner that does not interfere with the activity of betel leaf extract.

In still another embodiment, the additive is selected from nutrients such as proteins, carbohydrates and sugar, talc, magnesium sterate, cellulose, calcium carbonate, starch-gelatin paste and/or pharmaceutically acceptable carriers.

In still another embodiment, the betel leaf extract is administered orally or intramuscularly.

In yet another embodiment, the oral route is in the form of capsule, syrup, concentrate, powder or granules.

In yet another embodiment, the ratio of betel leaf extract to the additive is in the range between 10 to 1.

In yet another embodiment, the betel leaf extract is administered at a dosage level between 10 to 20 mg/kg of body weight for alternate days for one month.

In yet another embodiment, the betel leaf extracts reduce the viability of *L. donovani* promastigotes in vitro by 57 to 79% and reduce splenic and liver parasite load by 93 to 95%.

In yet another embodiment of the present invention, the betel leaf extract or composition is used for the treatment of visceral leishmaniasis or kala-azar.

In yet another embodiment of the present invention, the betel leaf extract or lyophilized extract or composition is administered together with or associated with a pharmaceutically acceptable additive.

In yet another embodiment of the present invention, the additive is selected in such a manner it does not interfere with the activity of betel leaf extract.

In yet another embodiment of the present invention, the additive is selected from nutrients such as proteins, carbohydrates, sugar and pharmaceutically acceptable carriers.

In yet another embodiment of the present invention, the betel leaf extract or the composition is administered orally or intramuscularly.

In still another embodiment, the oral route is in the form of capsule, syrup, concentrate, powder or granules.

In yet another embodiment of the present invention, the ratio of betel leaf extract to the additive is in the range between 10 to 1.

In still another embodiment of the present invention, the betel leaf extract is administered at a dosage level between 10 to 20 mg/kg of body weight for alternate days for one month.

In yet another embodiment of the present invention, the betel leaf extracts reduce the viability of *L. donovani* promastigotes in vitro by 57 to 79% and reduce splenic and liver parasite load by 93 to 95%.

In yet another embodiment of the present invention, a method of treating visceral leishmaniasis or kala-azar by administering a pharmaceutically acceptable composition of betel leaves extract or lyophilized extract.

In still another embodiment, the betel leaf extract is obtained by crushing the betel leaf or extracting the crushed leafs with water or organic solvents such as alcohol, carbontetrachloride, chloroform and acetone.

One more embodiment of the present invention relates to the preparation of betel leaf extracts comprising the following steps;

washing of the fresh leaves of *Piper betle* and homogenizing in a mixture blender;

sonicating in an ultrasonic bath with 2 to 3 bursts each for 15 minutes and filtering the extract, if desired repeating the extraction at least once and drying; and lyophilizing the extract to get a semi-solid mass In another embodiment of the invention, the betel leaf (*Piper betle*) is selected from Wild type, Climber type, Bangla type and Sweet type.

Effect of Betel Leaf Extract on the Viability of *L. donovani* Promastigotes in Vitro Extract prepared from wild type, Bangla type, and sweet type betel leaves are almost equally effective in reducing the viability of *L. donovani* promastigotes in a dose dependent manner (Table 1). Extracts from wild type betel leaf at a final concentration of 12-mg/ml reduce the viability of *L. donovani* promastigotes by 79%. On the other hand, extract from Bangla type or sweet type betel leaf at the same concentration i.e. 12 mg/ml reduces promastigote viability by 57.5% and 68.9% respectively. Thus, wild type betel leaf extract appears to have slightly more anti leishmanial activity than other type of betel leaf extract.

BRIEF DESCRIPTION OF THE ACCOMPANYING DRAWINGS

FIG. 1: Photomicrographs of Glemsa stained liver and spleen smears of *L.donovani* infected golden hamsters after treatment with PBS and betel leaf extract.

The following examples are given by way of explanation and for illustration only and these examples should not be construed in any manner to limit the scope of the invention.

EXAMPLES

Example 1

34.14 gm of fresh leaves of *Piper betle* thoroughly washed in sterile water was homogenized with 100 ml of glass distilled water in a mixture-blender. It was then sonicated in an ultrasonic bath with 3 burst each for 15 min. The extract was filtered through Whatman No.1 filter paper and the filtrate was collected. This process of extraction was repeated three times. The combined extract was lyophilized yielding a semi-solid mass weighing 1.17 gm. This was then tested for biological activity.

Example 2

The fresh leaves of *Piper betle* weighing 21.68 gm homogenized with distilled water (60 ml) in a mixture—blender and then sonicated in an ultrasonic bath with 2 burst each for 15 min. It was allowed to be extracted overnight or 16 hours. Filtering through Whatman No.1 filter paper separated the material extracted in water. This type of treatment for extraction was repeated for three times. The combined extract was evaporated to dryness in a flash evaporator under reduced pressure at 45° C. The residual substance was then dried in a desiccator under high vacuum and the semi-solid mass weighing 0.59 gm was tested for biological activity.

Properties of the Materials

The biologically active material obtained by examples 1 and 2 has the following properties:

i. The dried semisolid prepared as stated above was a dark colored material soluble in water and dimethyl sulfoxide.

ii. Thin layer chromatography of the active material shows five spots having $R_f$ 0.75, 0.64, 0.50, 0.40 and 0.33 in the solvent system of n-butanol, acetic acid and water in the ratio of 9:5:7 respectively.

iii. The HPLC analysis of the active material using Intersil ODS-3 (4.6×250 mm) analytical column, solvent system methanol and water in the ratio of 4:1 and a flow rate of 1.0 ml/min., detection at 217 nm resolved the material into eleven peaks with the retention time of 2.69, 4.27, 5.95, 6.97, 7.49, 9.39, 11.20, 12.40, 15.53, 18.90 and 21.49 min.

Example 3

Parasite: *L. donovani* strain AG83 was originally obtained from an Indian Kala-azar Patient (Ghosh, A. K., Bhattacharaya, F. K. & Ghosh, D. K. 1985. *Leishmania donovani:* amastigote inhibition and mode of action of berberine. Experimental Parasitology, 60: 404–13) and maintained in golden hamsters. Amastigotes were isolated from spleens of *L. donovani* infected golden hamsters as described (Jaffe, C. L., Grimaldi, G. & Mcmohan—Pratt, D. 1984. In genes and Antigens of parasite: A Laboratory manual, $2^{nd}$ $ed_n$ [moral, C. M., Ed.], P.47, Rio de Janiero). The spleen was rinsed in ice cold PBS—glucose (55 mm)/EDTA (2 mm), then lightly homogenized, macroscopic particles were allowed to settle, and the turbid suspension was decanted. This suspension was centrifuged at 100 g for 10 min at 4° C. The amastigote—enriched suspension was centrifuged at 800 g for 10 min. The pellet was suspended in 45% per coll (8.0 ml), and finally 25% per coll (4.0 ml) was layered over the amastigote suspension and centrifuged at 5000 g for 1 hr. The band containing amastigote was then taken and washed with PBS, and finally re-suspended in medium—199 (Gibco Laboratories, New York, N.Y., U.S.A.) supplemented with 20% FBS. Promastigotes were obtained by transforming amastigotes and were maintained in vitro in Medium—199 supplemented with 8% FBS.

Example 4

In vitro growth of *L. donovani* promastigote in the presence of betel leaf extract $0.5 \times 10^6$ *L. donovani* promastigotes in a total volume of 250 µl M-199+10% FBS were incubated with graded concentrations of betel leaf extract for 24 hr at 22° C. Cells were then checked microscopically for viability.

Effect of Betel Leaf Extract on the Viability of *L. donovani* Promastigotes in Vitro Water extract is prepared from the following types of betel leaf (*Piper betle*)

1. Wild type
2. Climber type
3. Bangla type
4. Sweet type

Extract prepared from wild type, Bangla type, and sweet type betel leaves are almost equally effective in reducing the viability of *L. donovani* promastigotes in a dose dependent manner (Table 1). Extracts from wild type betel leaf at a final concentration of 12-mg/ml reduce the viability of *L. donovani* promastigotes by 79%. On the other hand, extract from Bangla type or sweet type betel leaf at the same concentration i.e. 12 mg/ml reduces promastigote viability by 57.5% and 68.9% respectively. Thus wild type betel leaf extract appears to have slightly more antileishmanial activity than other type of betel leaf extract.

TABLE 1

Betel leaf extracts reduce the viability of *L. donovani* promastigotes in vitro

| Incubated with Medium | Dose (mg/ml) | Percent reduction of viability |
|---|---|---|
| Wild type betel leaf extract | 12.00 | 79.0 |
| | 8.0 | 67.0 |
| | 4.0 | 57.0 |
| Bangla type betel leaf extract | 12.0 | 65.3 |
| | 8.0 | 60.0 |
| | 4.0 | 57.5 |
| Sweet type betel leaf extract | 12.0 | 68.9 |
| | 8.0 | 63.8 |
| | 4.0 | 63.8 |

Example 5
Antileishmanial Activity of Betel Leaf Extract in Vivo

In vivo determination of antileishmanial activity of betel leaf extract in golden hansters. Golden hamsters (4–6 weeks old) were infected by intracardiac injection of freshly prepared *L. donovani* amastigotes ($1 \times 10^7$/hamster). One day post-infected hamsters were divided into three groups (5 animals per group); one group received intramuscular injection of wild type betel leaf extract (10 mg/kg body weight every other day), each animal received a total of 15 injections. Animals of the group received wild type betel leaf extract through oral route at the same dose (10-mg/kg body weight every other day. Animals in the control group received PBS by oral feeding every other day. Animals of all groups were killed one week after the last treatment i.e. 5 weeks post infection period. The splenic and liver parasite load was determined from impression smears after Giemsa staining. Results are expressed as the total parasite load per organ using the formula:

Organ weight in mg×the number of amastigotes per cell nucleus×$[2 \times 10^5]$

Betel leaf extract at a concentration of 10 mg/kg body weight was effective in reducing splenic and liver parasite load of *L. donovani* infected hamsters. Both routes i.e. intramascular and oral were equally effective. The type percent reduction of parasite burden varied between 93 to 95% using these two routes. The results were shown in table—2 and FIG. 1.

TABLE 2

Treatment of *L. donovani* infected golden hamsters with betel leaf extracts.

| Treatment with | Route of administration | Total parasite load ($\times 10^7$) | |
|---|---|---|---|
| | | LIVER | SPLEEN |
| PBS | Oral | 82.6 ± 63.1* | 10.6 ± 6.9 |
| Wild type betal leaf extract | Oral | 4.5 ± 3.0 | 0.7 ± 0.3 |
| | Intramuscular | 3.7** | 0.6 ± 0.5 |

*Mean ± S.D. from three to five animals
**Mean of two animals

As shown in Table—2 and FIG. 1, betel leaf extract at a concentration of 10 mg/kg body weight was effective in reducing splenic and liver parasite load of *L. donovani* infected hamsters. Of note, both routes i.e. intramascular or oral were almost equally effective. The type percent reduction of parasite burden varied between 93 to 95% using these two routes.

What is claimed is:
1. A method of treating visceral leishmaniasis or kala-azar in mammals, said method comprising the step of adminis- tering to the mammals a pharmaceutical composition comprising an effective amount of a betel leaf extract, wherein the betel leaf extract is obtained by crushing the betel leaf or extracting the crushed leafs with water or organic solvents selected from the group consisting of alcohol, carbon tetrachloride, chloroform and acetone.

2. The method according to claim 1, wherein the composition comprises betel leaf extract and a pharmaceutically acceptable additive.

3. The method according to claim 2, wherein the additive is selected from the group consisting of proteins, carbohydrates, sugar, talc, magnesium state, cellulose, calcium carbonate, starch-gelatin paste, pharmaceutically acceptable carriers, excipient, diluent and solvent.

4. The method according to claim 1, wherein the composition is administered orally or intramuscularly.

5. The method according to claim 1, wherein the oral route is administered in the form of capsule, syrup, concentrate, powder or granules.

6. The method according to claim 2, wherein the ratio of betel leaf extract to the additive is in the range between 1–10 to 10–1 by weight.

7. The method according to claim 1, wherein the composition is administered at a dosage level between 10 to 20 mg/kg of body weight for alternate days for one month.

8. The method according to claim 1, wherein administering the composition reduces the viability of *Leishmania donovani* promastigotes in vitro by 57 to 79% and reduces splenic and liver parasites load by 93 to 95%.

* * * * *